United States Patent [19]

Sears

[11] 4,097,503

[45] Jun. 27, 1978

[54] PHOSPHATIDYL PHOSPHONIUM HYDROXIDE COMPOUNDS

[76] Inventor: Barry D. Sears, 43 Bay State Road, Boston, Mass. 02215

[21] Appl. No.: 770,290

[22] Filed: Feb. 22, 1977

Related U.S. Application Data

[63] Continuation-in-part of Ser. No. 731,132, Oct. 12, 1976.

[51] Int. Cl.$^2$ ............................................... C08H 3/00
[52] U.S. Cl. ..................................... 260/403; 260/931
[58] Field of Search ................................ 260/403, 931

[56] References Cited

U.S. PATENT DOCUMENTS

| | | | |
|---|---|---|---|
| 3,214,434 | 10/1965 | Grayson | 260/931 X |
| 3,654,342 | 4/1972 | Gillham et al. | 260/403 X |

OTHER PUBLICATIONS

Anjea et al., Biochem. Biophys. Acta. 248, 455–457 (1971).
Dawson, R., Biochem. J. 102, p. 76 (1967).
Sears, B. et al., Biochem. Biophys. Res. Comm. 60, pp. 1141–1147 (1974).
Chandra, J., Chem. Phys. Lipids 4, pp. 104–108 (1970).

*Primary Examiner*—Winston A. Douglas
*Assistant Examiner*—John F. Niebling
*Attorney, Agent, or Firm*—Richard P. Crowley

[57] ABSTRACT

Novel synthetic phosphatidyl phosphonium hydroxide compounds are prepared which have a hydrophobic/hydrophilic balance different from the natural phosphatidylcholine, which alterations are carried out by changes in the quaternary phosphonium polar group to provide different surfactant properties.

10 Claims, No Drawings

PHOSPHATIDYL PHOSPHONIUM HYDROXIDE COMPOUNDS

REFERENCE TO PRIOR APPLICATION

This application is a continuation-in-part of application Serial No. 731,132, filed Oct. 12, 1976.

BACKGROUND OF THE INVENTION

This invention relates to novel chemical compounds structurally related to phosphatidylcholine, to a method of preparing such compounds, and to the use as surfactants of such chemical compounds with or for compounds which have limited or no solubility in aqueous solutions.

Phospholipids and phosphatidylcholine in particular are amipathic compounds in that they consist of hydrophobic and hydrophilic groups or regions within the same molecule. Compounds with this amipathic property tend to self-associate in aqueous systems to form micelles which have a hydrophobic interior and a hydrophilic exterior. As a result, these compounds act as surfactants and can solubilize other relatively aqueous insoluble compounds which have limited or no solubility in water, and can partition such insoluble compounds into the hydrophobic region of the micelle. The external polar hydrophilic region of the micelle confers water solubility on the micelle complex or group. It has been well known that such nonsoluble biological compounds, such as cholesterol, cholesterol esters and derivatives, triglycerides and other compounds, can be solubilized in phospholipid micelles. However, the extent of solubilizing power of any surfactant is highly dependent on the ratio of hydrophobic-to-hydrophilic balance within the particular molecule.

For example, natural phosphatidylcholine (that is, lecithin) is an excellent emulsifying agent for a number of insoluble biological compounds, such as cholesterol, cholesterol esters and triglycerides, and lecithin is widely used in many industrial applications; for example, the food industry. Lecithin is a natural surfactant, and, like other such surfactants, its solubilization properties are derived from its amipathic character; that is, the molecule possesses a region of hydrophobic character (the hererogeneous fatty-acid chain) and a region of hydrophilic character (the polar head group-ethyl-N-trimethyl ammonium group). In addition, lecithin is zwitterionic in the pH range of 2-12, because it possesses a positively charged group (the quaternary ammonium group) and a negatively charged group (the phosphate group). This zwitterionic character stabilizes the ionic structure of the lecithin against any pH fluctuations that would tend to flocculate other natural detergents; that is, other phospholipids or bile salts.

The natural-occurring phospholipids are limited in solubilizing properties. For example, it is known that the maximum amount of cholesterol that phosphatidylcholine can solubilize is in a molar ratio of about one to one, while little, if any, cholesterol ester can be solubilized by phosphatidylcholine. Thus, novel phospholipid compounds which have modified solubilized properties (particularly those which solubilize a greater amount of both biological and industrial compounds than is possible with the natural compound or have different solubilized properties) would be most desirable and useful.

SUMMARY OF THE INVENTION

My invention relates to novel, synthetic, phosphatidyl phosphonium compounds, particularly phosphonium hydroxide compounds, which are characterized by enhanced or different solubilizing, surfactant and other properties from the heterogeneous, natural-occurring phosphatidylcholine, to the method of preparing such compounds and to the method of using such compounds as surfactants to solubilize and emulsify other compounds, particularly cholesterol and cholesterol-derived compounds and triglyceride compounds.

I have discovered in particular that the solubilizing or surfactant properties of my novel phosphatidyl compounds can be obtained by variation in the separation of the positively and negatively charged groups; that is, by increasing or decreasing the distance between the groups, such as by increasing or decreasing the number of methylene groups between the charged moieties and/or by delocation of the positive charge on and about the quaternary phosphorous atom, such as by replacing one or more of the three methyl groups with other groups, such as with other alkyl groups. Thus, by taking advantage of the zwitterionic nature of natural phosphatidylcholine and changing the structure to produce novel compounds, modified and, in some cases, unexpected surfactant properties are obtained, particularly by the alteration and modification of the polar head group (the quaternary phosphonium) and region of the various phosphatidylcholines.

My new compounds are useful and interesting substitutes for lecithin in solubilizing nonaqueous soluble compounds, and in particular such new compounds may be useful in the regression of atherosclerotic lesions and as antiatherosclerotic agents in blood or other biological fluids, and as stabilizing agents and emulsifiers, particularly in food products.

The novel synthetic phosphatidyl phosphonium compounds of my invention are represented by the formula:

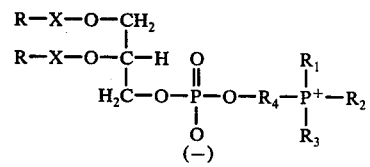

wherein X is a carbonyl group (C=O); R is a hydrocarbon radical; for example, a long-chain radical, either the same or different, straight or branch chain, and preferably a $C_{14}$ to $C_{20}$ fatty-acid/alcohol radical; $R_1$, $R_2$ and $R_3$ are hydrocarbon radicals, such as alkyl, alkylene, phenyl or alkyl-substituted phenyl radicals, and preferably are lower alkyl radicals; for example, $C_1$–$C_4$, such as methyl, ethyl, propyl, isopropyl, butyl and isobutyl radicals or a phenyl or benzyl radical, with $R_1$, $R_2$ and $R_3$ being the same or different radicals; and $R_4$ is a hydrocarbon radical, preferably a long-chain hydrocarbon radical of from 1 to 10 carbon atoms; for example, 1 to 5, such as alkyl or alkylene radicals, straight or branch chain, except for the compound where $R_1$, $R_2$ and $R_3$ are methyl and $R_4$ is an ethyl radical. Most preferably $R_4$ is a $C_2$–$C_5$ methylene chain, and has a different number of carbon atoms than $R_1$, $R_2$ and $R_3$. The glycerol backbone of the compounds may have the d, l or racemic configuration.

Some preferred phosphatidyl phosphonium hydroxide compounds of my invention are represented by:

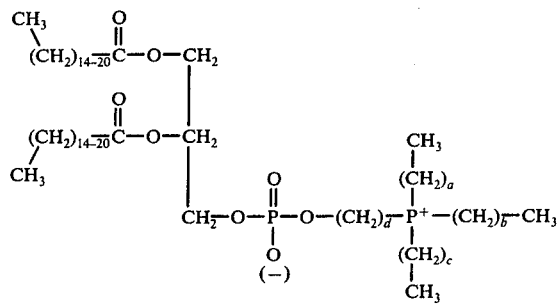

Typical compounds include:
I: a = b = o c = 1 d = 2
II: a = b = c = o d = 4
III: a = b = c = o d = 3
IV: a = b = o c = 2 d = 2

In my compounds, the R radicals may vary and be composed of natural or synthetic fatty radicals, but preferably are $C_{14}$ to $C_{20}$ fatty acid or alcohol radicals, or combinations and mixtures thereof. The fatty radicals useful include both saturated and ethylenically unsaturated hydrocarbon radicals, such as those radicals derived from fatty acid or alcohols, such as, for example, myristate, palmitate, oleate, linoleate and stearate radicals and heterogeneous mixtures, such as found in natural products like egg yolk, soybeans and the like. The R and X radicals may be the same or different radicals, but preferably are the same X radicals with the same or different R radicals. In one method of preparation, as hereinafter described, the R radicals will be those radicals of the quaternary phosphonium alcohol selected for the reaction. By the selection of desired fatty radicals and the length thereof, the hydrophobic character of this portion of the synthetic compound may be altered and modified to a desired defined level, such as by selecting the R radical to be the same or different chain length or degree of saturation or substitution.

The polar group or quaternary phosphonium group of my compounds may be composed of substituent radicals to alter the electropositive character of the quaternary phosphonium atom, but particularly are $C_1$–$C_4$ alkyl radicals.

My novel compounds would include, but not be limited to: dioleate phosphatidyl-(isopropyl-N-triethyl) phosphonium hydroxide; dipalmitate phosphatidyl-(ethyl-N-dimethyl, ethyl) phosphonium hydroxide; distearyl phosphatidyl-(ethyl-N-dimethylethyl) phosphonium hydroxide; oleate-palmitate phosphatidyl-(ethyl-N-dimethylethyl)-phosphonium hydroxide; dimyristate phosphatidyl-(butyl-N-dipropylmethyl) phosphonium hydroxide; dipalmitate phosphatidyl-(propyl-N-trimethyl) phosphonium hydroxide; egg phosphatidyl-(propyl-N-trimethyl) phosphonium hydroxide; soybean phosphatidyl-(propyl-N-trimethyl) phosphonium hydroxide; and mixtures thereof.

My compounds have been described employing derived nomenclature. However, for example, dimyristate phosphatidyl-(butyl-N-dipropylmethyl) phosphonium hydroxide above also may be named as dimyristoyl phosphatidyl-(tetramethylene-P-dipropylmethyl) quaternary phosphonium, and the other named compounds may be described similarly.

My compound may be prepared by a variety of methods. However, the preferred method of preparation is to prepare the synthetic phosphatidyl alkyl phosphonium hydroxide by reacting and coupling the polar head group moiety to phosphatidic acid; for example, using triisopropylbenzenesulfonyl chloride in pyridine (see R. Anjea and J. S. Chandra, Biochem. Biophys. Acta 248, 455 (1971) and B. Sears, W. C. Hutton, and T. E. Thompson, Biochem. Biophys. Res. Comm. 60, 1141 (1974). The phosphatidic acid may be derived from natural or synthetic phosphatidylcholine by the digestion with the enzyme phospholipase D (see R. M. C. Dawson, Biochem. J. 102, 76 (1967). The modified polar head group compound is then synthesized by the general reaction method represented as follows:

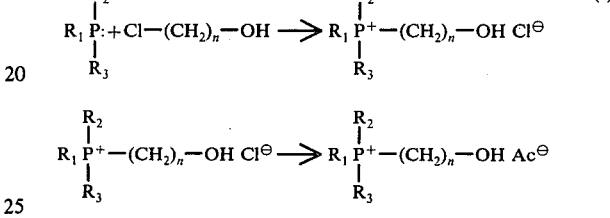

The salt form (for example the acetate form) of the quaternary phosphonium salt is obtained by ion-exchanging the quaternary phosphonium halide salt (for example the chloride form) in an ion-exchange column equilibrated with the acetate ions. Thus, my method is: to synthesize synthetic phosphatidylcholine or isolate natural phosphatidylcholine; then enzymatically to cleave the phosphatidylcholine to phosphatidic acid; to synthesize a modified hydroxy quaternary alkyl phosphonium halide, convert the quaternary hydroxy alkyl phosphonium halide to the corresponding acetate (the acetate form is more soluble than the halide form in pyridine, the solvent used for coupling) and covalently couple with quaternary alkyl phosphonium acetate onto the phosphatidic acid, thereby giving the phospholipid modified in the polar head group. The acetate or weak-acid form may also be used with acetonitrile as the solvent or the iodide form used where the coupling solvent is about a one:one mixture of pyridine and acetonitrile.

My method of preparing synthetic phosphatidyl alkyl quaternary phosphonium compounds comprises covalently reaction or coupling in a common nonaqueous solvent typically an organic polar solvent like pyridine or acetonitrile; for example, a nitrogen-containing solvent, the quaternary phosphonium salt preferably the weak acid salt or halo salt of the alkyl phosphonium compound, with phosphatidic acid and recovering the phosphatidyl alkyl quaternary phosphonium hydroxide compound and chromatographically purifying the resulting compound.

My invention will be described for the purpose of explanation and illustration only in connection with the preparation of certain preferred compounds. However, it is recognized and is within the scope and intent of my invention and disclosure that other compounds and other methods of preparation can be formulated and used.

DESCRIPTION OF THE EMBODIMENTS

Synthesis of dipalmitoyl phosphatidyl phosphonium hydroxide compounds

Glycerol phosphoryl choline is derived from crude egg yolk phosphatidylcholine using the method of J. S. Chandra, Chem. Phys. Lipids 4 104 (1970). Dipalmitoyl phosphatidylcholine is synthesized according to the method of Cubero Robles, E. and van de Berg, D., Biochem. Biophys. Acta 187 520 (1969). Dipalmitoyl phosphatidic acid is prepared by the enzymatic cleavage of dipalmitoyl phosphatidylcholine by cabbage phospholipase D according to Dawson, R. M. C., Biochem. J. 102 76 (1967). The appropriate hydroxyl alkyl phosphonium acetate is covalently linked to the dipalmitoyl phosphatidic acid using 2,4,6 triisopropylbenzenesulfonyl chloride as a coupling agent as described by Sears et al, Biochem. Biophys. Res. Comm. 60 1141 (1974). The phosphatidylcholine analog is then purified by silicic acid chromatography. The detailed synthetic description of the hydroxy alkyl phosphonium compounds and the corresponding phosphatidylcholine compounds is described below.

A. Dipalmitoyl phosphatidyl-(ethyl-P-triethyl) phosphonium hydroxide (I).

0.4 moles of triethyl phosphine and 0.5 moles of 2-chloro-ethanol are dissolved in 200 ml of ether and allowed to sit for 24 hours at room temperature in the dark. The precipitated 2-hydroxy ethyl-P-(triethyl) phosphonium chloride is filtered off and dissolved in 50 ml of water. The solution is placed on a 2 × 40 cm column of Bio Rad AGl-X8 cation-exchange column in the acetate form. The column is eluted with distilled water. The (2-hydroxy ethyl) P-triethyl phosphonium acetate is concentrated by dryness. 500 moles of the (2-hydroxy ethyl)-P-triethyl phosphonium acetate in methanol is mixed with 300 micro moles of dipalmitoyl phosphatidic acid and then taken to dryness. The mixture is dried under high vacuum against $P_2O_5$ overnight. 800 micro moles of 2,4,6 triisopropylbenzenesulfonyl chloride in 10 ml of dry pyridine is added to the dry mixture. The reaction mixture is stoppered and heated and stirred for 1 hour at 65° C and then stirred for 4 hours at room temperature. At the end of the reaction, the pyridine is evaporated from the reaction. The residue is taken up in 20 ml of chloroform-methanol (2:1) and then 5 ml of distilled water is added. The resulting lower phase is taken to dryness and the residue is taken up in chloroform. The chloroform solution is applied to 2 × 30 cm silicic acid column and the phospholipid eluted with increasing amounts of methanol in chloroform.

B. Dipalmitoyl phosphatidyl-(butyl-P-trimethyl) phosphonium hydroxide (II).

0.4 moles of trimethyl phosphine and 0.5 moles of 4-chloro-butanol are dissolved in 200 ml of ether and allowed to sit for 24 hours at room temperature in the dark. The precipitated 4-hydroxy ethyl-P-(trimethyl) phosphonium chloride is filtered off and then dissolved in 50 ml of water. The reaction mixture is purified as described for the (2-hydroxy ethyl)-P-triethyl phosphonium acetate. 500 micro moles of (4-hydroxy butyl)-P-trimethyl phosphonium acetate and 300 micro moles of dipalmitoyl phosphatidic acid are mixed in methanol and taken to dryness. The mixture is dried under high vacuum against $P_2O_5$ overnight. 800 micro moles of 2,4,6 triisopropylbenzenesulfonyl chloride in 10 ml of pyridine is added. The reaction is heated for 1 hour at 65° C and then stirred for 4 hours at room temperature. The reaction is then purified as described above.

C. Dipalmitoyl phosphatidyl-(propyl-P-trimethyl) phosphonium hydroxide (III).

0.4 moles of trimethyl phosphine and 0.5 moles of 3-bromo-propanol are dissolved in 200 ml of ether and allowed to sit for 24 hours at room temperature in the dark. The precipitated 3-hydroxy propyl)-P-trimethyl phosphonium chloride is filtered off and then dissolved in 50 ml of water. The (3-hydroxy propyl)-trimethyl phosphonium salt is converted to the acetate salt as previously described. 500 moles of (3-hydroxy propyl)-P-trimethyl phosphonium acetate and 300 moles of dipalmitoyl phosphatidic acid are mixed in methanol and evaporated to dryness. The residue is dried at high vacuum and against $P_2O_5$ for 12 hours. 800 moles of 2,4,6 triisopropylbenzenesulfonyl chloride in 10 ml of pyridine is added. The reaction is heated at 65° C for 1 hour and then stirred for 4 hours at room temperature. The dipalmitoyl phosphatidyl(propyl-P-trimethyl) phosphonium hydroxide is purified as previously described.

D. Dipalmitoyl phosphatidyl-(ethyl-P-tripropyl) phosphonium hydroxide (IV).

0.4 moles of tripropyl phosphine and 0.5 moles of 2-bromo-ethanol are dissolved in 200 ml of ether and allowed to sit for 24 hours at room temperature in the dark. The precipitated 2-hydroxy ethyl-P-tripropyl phosphonium chloride is filtered off and then dissolved in 50 ml of water. The (2-hydroxy)-P-tripropyl phosphonium acetate is purified as previously described. 500 moles of (2-hydroxy)-P-trimethyl phosphonium acetate and 300 moles of dipalmitoyl phosphatidic acid are mixed in methanol and taken to dryness. The residue is dried under high vacuum and against $P_2O_5$ overnight. 800 moles of 2,4,6 triisopropylbenzenesulfonyl chloride in 10 ml of pyridine is added to the residue. The mixture is heated for 1 hour at 65° C and then stirred for 4 hours at room temperature. The purification of the dipalmitoyl phosphatidyl-(ethyl-P-tripropyl) phosphonium hydroxide is carried out as previously described.

I have described the synthesis of a selected number of preferred phosphatidylcholine compounds in which the hydrophilic region of the molecule has been chemically modified. As a result, the hydrophobic-to-hydrophilic balance within the molecule is altered. Furthermore, the charge density of the positively charged phosphonium atom is significantly different from that of the quaternary ammonium atom usually found in phosphatidylcholine.

These new compounds have utility as solubilizing agents in food-processing, industrial and biological applications. In addition, because of their close structural relation to phosphatidylcholine, they also find application in clinical medicine, such as the regression of atherosclerotic lesions, via the solubilization of deposited cholesterol.

What I claim is:

1. Synthetic phosphatidyl quaternary phosphonium compounds represented by the formula:

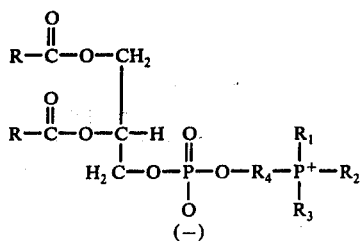

wherein R is a long-chain hydrocarbon radical; $R_1$, $R_2$ and $R_3$ are $C_1$–$C_4$ alkyl radicals, phenyl radicals or benzyl radicals; $R_4$ is a methylene radical of from 1 to 10 carbon atoms, except where $R_4$ is dimethylene and $R_1$, $R_2$ and $R_3$ are methyl radicals.

2. The compounds of claim 1 wherein R is a $C_{14}$–$C_{20}$ fatty radical.

3. The compounds of claim 1 wherein both R radicals are the same.

4. The compounds of claim 1 wherein $R_1$, $R_2$ and $R_3$ are the same methylene radical and $R_4$ is a different alkyl radical.

5. The compound of claim 1 selected from the group consisting of:

dioleoyl phosphatidyl-(methylethylene-P-triethyl)-phosphonium;

dipalmitoyl phosphatidyl-(ethylene-P-dimethylethyl)phosphonium;

distearoyl phosphatidyl-(ethylene-P-dimethylethyl)-phosphonium;

oleoyl-palmitoyl phosphatidyl-(ethylene-P-dimethylethyl)-phosphonium;

dimyristoyl phosphatidyl-(tetramethylene-P-dipropylmethyl)phosphonium;

dipalmitoyl phosphatidyl-(trimethylene-P-trimethyl)-phosphonium;

egg phosphatidyl-(trimethylene-P-trimethyl)phosphonium; soybean phosphatidyl-(trimethylene-P-trimethyl)phosphonium; and dipalmitoyl phosphatidyl-(tetramethylene-P-trimethyl)-phosphonium.

6. The compound of claim 1 wherein R is an ethylenically unsaturated hydrocarbon radical.

7. The compound of claim 1 wherein $R_1$, $R_2$ and $R_3$ are methyl radicals and $R_4$ is a tetramethylene radical.

8. The compound of claim 1 wherein $R_4$ is a $C_2$–$C_5$ methylene radical.

9. The compound of claim 1 wherein $R_4$ is a trimethylene radical and $R_1$, $R_2$ and $R_3$ are ethyl radicals.

10. The compound of claim 1 wherein

is a myristoyl, palmitoyl, oleoyl, linoleoyl, stearoyl, egg yolk or soybean radical.

* * * * *